US00PP28969P2

(12) United States Plant Patent
Benetka

(10) Patent No.: US PP28,969 P2
(45) Date of Patent: Feb. 20, 2018

(54) ***WEIGELA* PLANT NAMED 'VUKOZGEMINI'**

(50) Latin Name: *Weigela hybrida*
Varietal Denomination: VUKOZGEMINI

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,315

(22) Filed: Sep. 2, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne M Grunberg
(74) *Attorney, Agent, or Firm* — Cassandra Bright

(57) ABSTRACT

A new and distinct *Weigela* plant named 'VUKOZGEMINI' is disclosed, characterized by large white flowers which change to pink. Plants bloom profusely and exhibit re-blooming. Plants have a low growth habit. The new variety is a *Weigela*, normally produced as an outdoor garden plant.

3 Drawing Sheets

Latin name of the genus and species: *Weigela hybrida.*
Variety denomination: 'VUKOZGEMINI'.

BACKGROUND OF THE INVENTION

The new *Weigela* cultivar is a product of a planned breeding program conducted by the inventor, Vojtech Benetka in Pruhonice, Czech Republic. The objective of the breeding program was to produce new *Weigela* varieties with a low growth habit. The cross resulting in this new variety was made in 2004.

The seed parent is *Weigela* 'Musca', unpatented. The pollen parent is an unpatented, proprietary *Weigela* referred to as '99-19-254'. The new variety was identified as a potentially interesting selection in 2007, at a research nursery in Pruhonice, Czech Republic.

Asexual reproduction of the new cultivar 'VUKOZGEMINI' by softwood cuttings was first performed in 2007, at a research nursery in Pruhonice, Czech Republic. Subsequent propagation has shown that the unique features of this cultivar are stable and reproduced true to type in at least five successive generations.

SUMMARY OF THE INVENTION

The cultivar 'VUKOZGEMINI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VUKOZGEMINI' These characteristics in combination distinguish 'VUKOZGEMINI' as a new and distinct *Weigela* cultivar:

1. White flowers that change to pink.
2. Large flowers with profuse blooming.
3. Re-blooming of flowers.
4. Low growth habit.

PARENT COMPARISON

Plants of the new cultivar 'VUKOZGEMINI' are similar to plants of the seed parent in most horticultural characteristics, however, plants of the new cultivar 'VUKOZGEMINI' differ in the following;

1. New cultivar has white flowers which change to pink, whereas the parent has true pink flowers.

Plants of the new cultivar 'VUKOZGEMINI' are similar to plants of the pollen parent in most horticultural characteristics, however, plants of the new cultivar 'VUKOZGEMINI' differ in the following;

1. New cultivar has white flowers which change to pink, whereas the parent has true white flowers.

COMMERCIAL COMPARISON

Plants of the new cultivar 'VUKOZGEMINI' can be compared to the patented commercial variety *Weigela* 'Bokrasopea' (U.S. Plant Pat. No. 24,585). These varieties are similar in most horticultural characteristics; however 'VUKOZGEMINI' differs in the following:

1. New cultivar has larger flowers than this commercial variety.
2. New cultivar re-blooms less than this commercial variety.
3. New cultivar has flowers that open to the color white which fade to strong pink, whereas the commercial variety has its flowers open to the color white which fade only slightly to pink.

BRIEF DESCRIPTION OF THE PHOTOGRAPHS

The accompanying photograph in FIG. 1 illustrates in full color a typical plant of 'VUKOZGEMINI' grown in a 1 gallon container.

Figure 1:
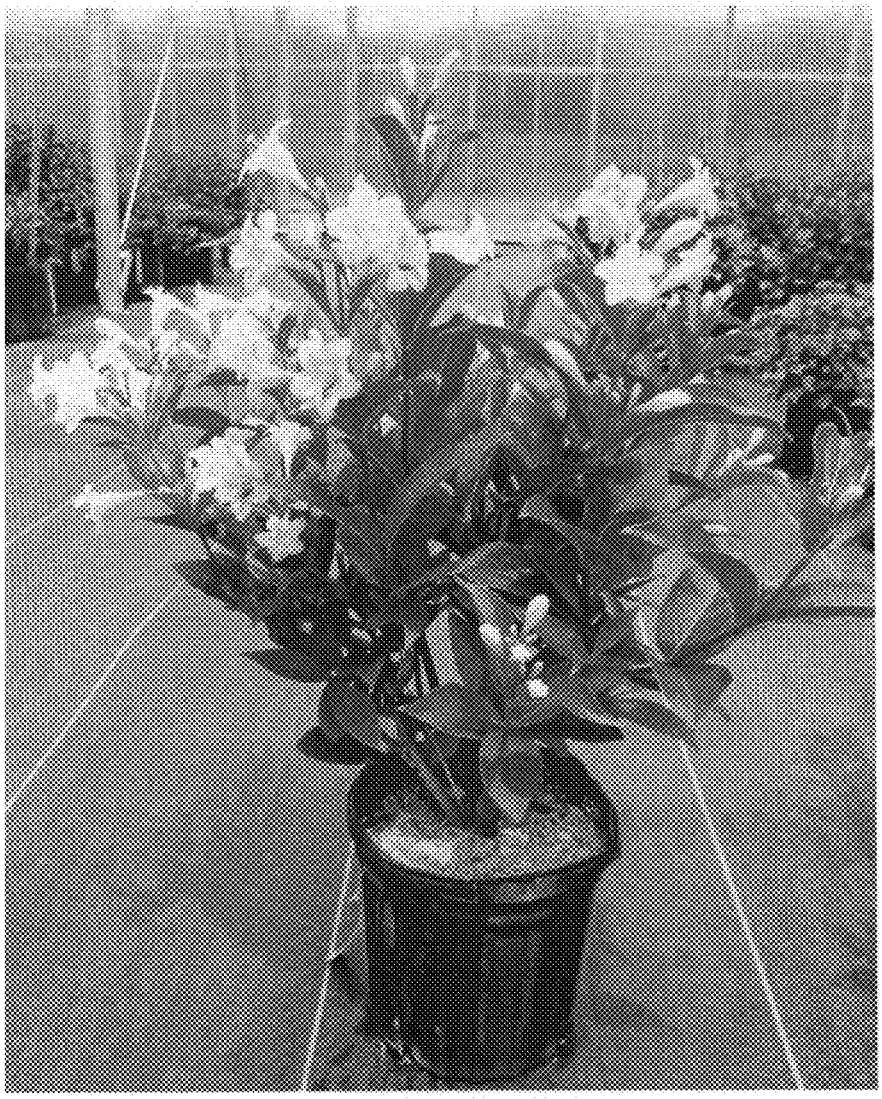
Figure 2:
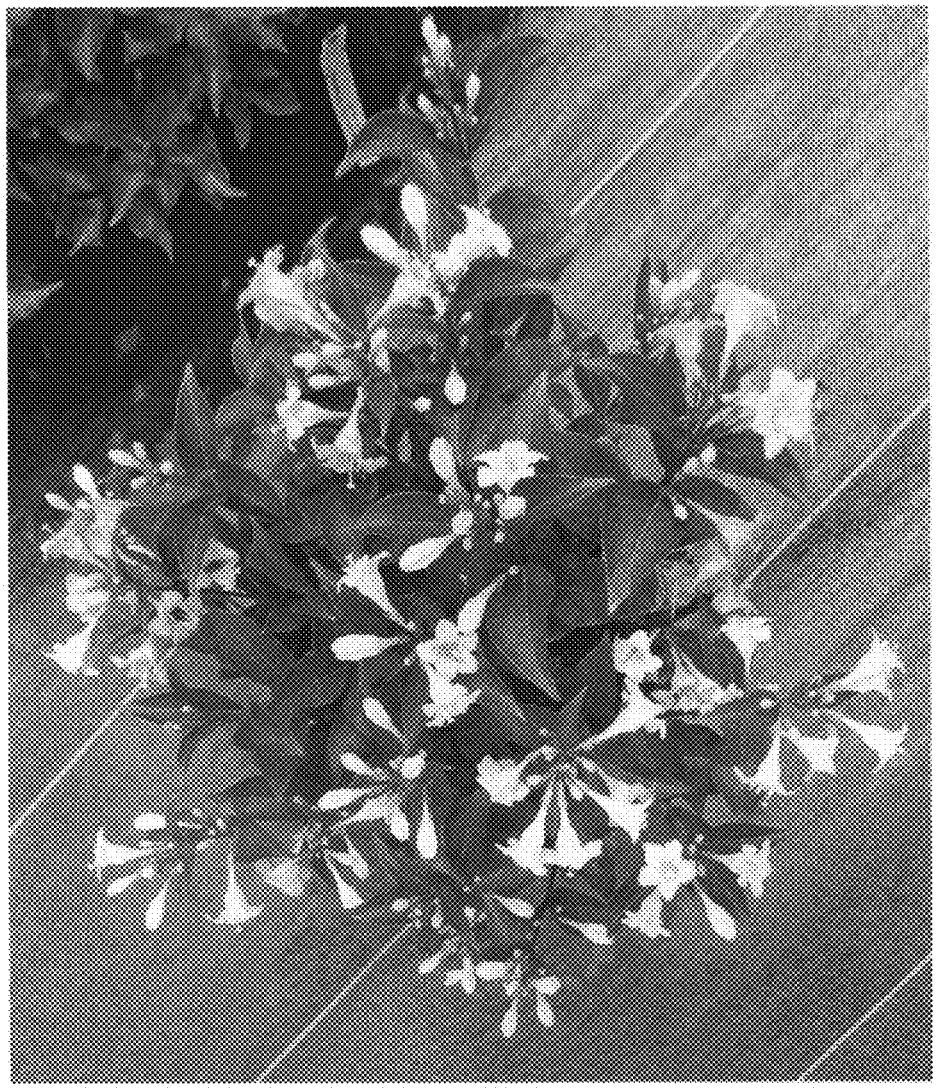
FIG. 2 illustrates a top view of the same plant. Age of the plant photographed is approximately 2 years.
Figure 3:
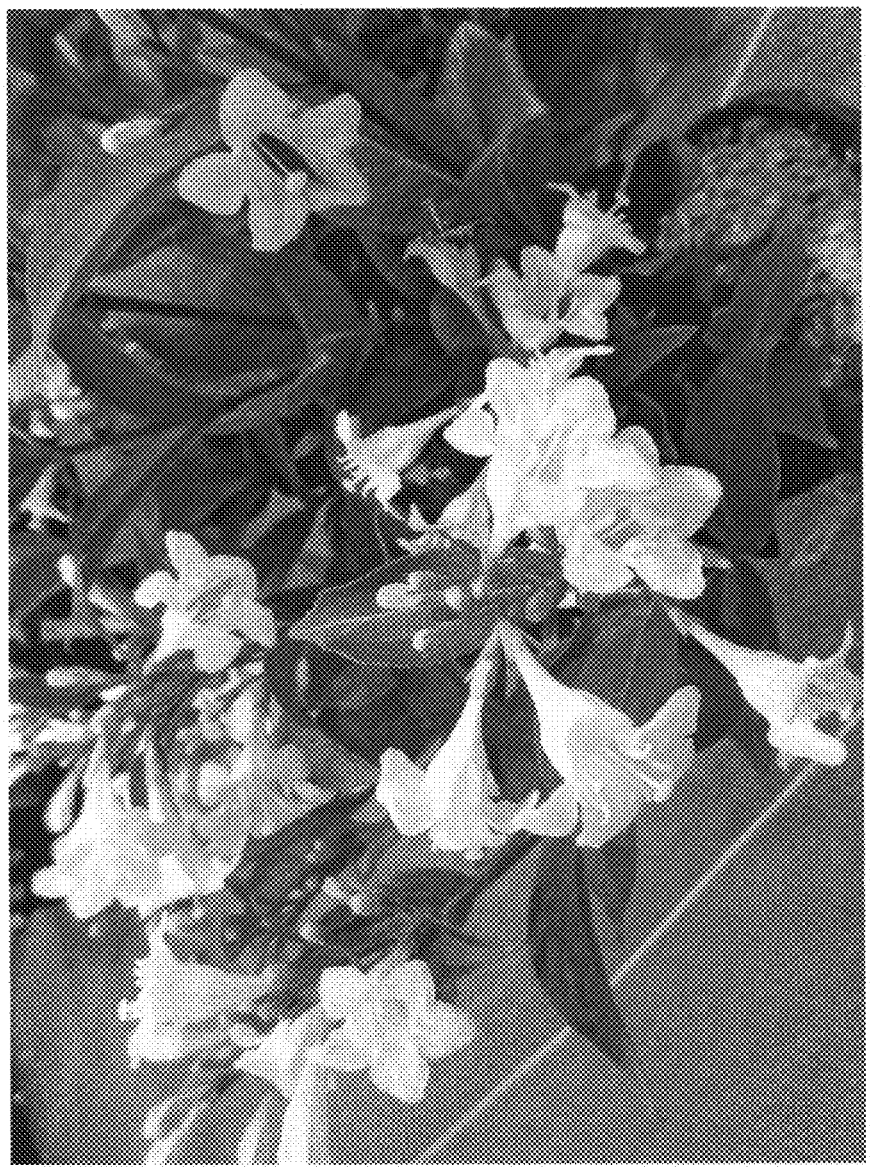
FIG. 3 illustrates a close up view of both white flowers and more mature flowers which have turned pink.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'VUKOZGEMINI' plants grown in a polyhouse in Grand Haven, Mich. Measurements were taken during late Spring. The plants were 2 years old. The growing temperature ranged from approximately 5° C. to 27° C. Measurements and numerical values represent averages of typical plant types.

Botanical classification: *Weigela hybrida* 'VUKOZGEMINI'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.
Age of plant described: Approximately 2 years old.
Growth habit: Medium, compact growth.
Pot size of plant described: 2 gallon container.
Overall plant shape: Upright and rounded.
Height: 89 cm.
Plant spread: 70 cm.
Growth rate: Medium.
Plant vigor: Strong.
Branching characteristics: Opposite.
Length of primary lateral branches: Average 65 cm.
Diameter of lateral branches: 8.5 mm.
Quantity of lateral branches: 40.
Stem:
- *Stem appearance*.—Round.
- *Stem strength*.—Strong.
- *Color*.—Near RHS Yellow-Green 144C.
- *Pubescence*.—Yes.

Internode length: Range is 3.5 to 5.6 cm.

FOLIAGE

Leaf:
- *Arrangement*.—Opposite.
- *Leaf shape*.—Ovate-oblanceolate.
- *Average length*.—Approximately 7.5 cm.
- *Average width*.—Approximately 3.9 cm.
- *Apex*.—Acute.
- *Base*.—Acute to cuneate.
- *Margin*.—Serrulate.
- *Texture of top surface*.—Slight pubescence.
- *Texture of bottom surface*.—Pubescent, to a greater degree than upper surface.
- *Color*.—Young foliage upper side: Near RHS Green 137A. Young foliage under side: Near RHS Green 139C. Mature foliage upper side: Near RHS Green 137A. Mature foliage under side: Near RHS Green 139C.
- *Venation*.—Pattern: Pinnate. Color upper side: Near RHS Yellow-Green 145A. Color under side: Near RHS Yellow-Green 145D.
- *Petiole*.—Length: 4.0 mm. Diameter: 2.0 mm. Petiole color upper side: Near RHS Yellow-Green 145A. Petiole color lower side: Near RHS Yellow-Green 145B. Petiole Texture: Pubescent.
- *Foliage durability*.—Very durable.

FLOWER

Natural flowering season: Late spring to summer.
Inflorescence type and habit: Umbel to panicle.
Inflorescence height: 11.0 cm.
Inflorescence width: 6.9 to 9.5 cm.
Quantity of flowers per inflorescence: 18 to 20.
Quantity of flowers per plant: 100 to 300 flowers and buds on a mature plant in full bloom.
Individual flowers:
- *Flower shape*.—Salverform.
- *Flower aspect*.—Upward and slightly outward.
- *Flowering arrangement*.—Single salverform flower.
- *Size*.—Diameter: Approximately 2.8 cm. Depth: Approximately 4.0 cm.
- *Flower other characteristics*.—Persistence: Self cleaning. Fragrance: Slight floral scent.

Bud:
- *Shape*.—Obovate-spatulate.
- *Length*.—2.1 cm.
- *Diameter*.—5.5 mm.
- *Color*.—Near RHS Yellow 2D mixed with near RHS Red-Purple 63D.

Petal:
- *Petal arrangement*.—Whorled, fused at opening of throat.
- *Number of petals per flower*.—5.
- *Petal shape*.—Obovate to oblanceolate.
- *Petal base*.—Fused at throat.
- *Margin*.—Entire, slightly undulate.
- *Tip shape*.—Obtuse.
- *Length*.—1.2 cm.
- *Width*.—1.0 cm.
- *Texture*.—Upper: Smooth. Lower: Smooth.
- *Flower tube*.—Length: 3.0 cm. Diameter, base: 2.0 mm.
- *Throat*.—Texture: Smooth. Color: First opening: Near RHS White 155B with one spot of Red 44D. Fully open: Near RHS White 155B with hints near RHS Red-Purple 64A and one spot near RHS Red-Purple 60A. Fades to: Near RHS Red-Purple 60C with one spot near RHS Red-Purple 59A.
- *Color*.—When opening: Upper surface: Near RHS White 155B. Lower surface: Near RHS White 155B. Fully opened: Upper surface: Near RHS White 155B slightly blended with Red-Purple Group 64B. Lower surface: Near RHS White 155B slightly blended with Red-Purple Group 64B.

Sepal:
*Arrangement*.—Unguiculate, fused at base.
*Appearance*.—Long, narrowly triangular.
*Number*.—5.
*Shape*.—Narrowly triangular.
*Tip*.—Acute.
*Base*.—Obtuse.
*Margin*.—Entire.
*Length*.—8.0 mm.
*Width*.—1.0 mm.
*Texture, upper*.—Smooth, coriaceous.
*Texture, lower*.—Smooth, coriaceous.
*Color*.—Upper surface at maturity: Near RHS Yellow-Green 144C. Under surface at maturity: Near RHS Yellow-Green 144C.

Peduncle:
*Length*.—1.0 cm.
*Diameter*.—1.0 mm.
*Color*.—Near RHS Yellow-Green 144A.
*Orientation*.—Upright/outward.
*Strength*.—Good.
*Texture*.—Smooth, coriaceous, slightly pubescent.

Pedicel:
*Length*.—1.3 cm.
*Diameter*.—1.5 mm.
*Angle*.—Upright and outward.
*Strength*.—Good.
*Texture*.—Smooth, coriaceous, slightly pubescent.
*Color*.—Near RHS Yellow-Green 144A.

REPRODUCTIVE ORGANS

Stamens:
*Number*.—5.
*Filament length*.—3.0 cm.
*Filament color*.—Near RHS White 155B.

Anthers:
*Shape*.—Linear, slightly oblong.
*Length*.—5.0 mm.
*Color*.—Near RHS White 155B fades to RHS Red-Purple 63D with age.
*Pollen color*.—Near RHS White 155B.
*Pollen amount*.—Some.

Pistil:
*Number*.—1 per flower.
*Length*.—3.6 cm.
*Style*.—Length: 3.5 cm. Color: Near RHS White 155B.
*Stigma*.—Color: Near RHS Yellow 2D. Shape: Globular, flat-bottomed.

OTHER CHARACTERISTICS

Seeds and fruits: Not observed.

Disease/pest resistance: Neither resistance nor susceptibility to normal diseases and pests of *Weigela* have been observed aside from mildew resistance.

Temperature tolerance: The new variety has been observed to tolerate temperatures between −31° C. to 38° C.

Environmental stressors: Good resistance to wind and rain.

What is claimed is:

1. A new and distinct cultivar of *Weigela hybrida* plant named 'VUKOZGEMINI' as herein illustrated and described.

* * * * *